United States Patent [19]
Martens et al.

[11] Patent Number: 5,804,417
[45] Date of Patent: Sep. 8, 1998

[54] RECOMBINANT PRODUCTION OF PROTEINS USING 7B2 PROTEIN

[75] Inventors: Gerardus Julianus Maria Martens, Nijmegen, Netherlands; Bhabatosh Chaudhuri, Münchenstein, Switzerland; Christine Stephan, Kingersheim, France

[73] Assignee: Novartis Corporation, Summit, N.J.

[21] Appl. No.: 709,915

[22] Filed: Sep. 9, 1996

Related U.S. Application Data

[62] Division of Ser. No. 244,492, Sep. 2, 1994, Pat. No. 5,708,140.

[30] Foreign Application Priority Data

Nov. 29, 1991 [NL] Netherlands ............... 9102009

[51] Int. Cl.⁶ .............. C07K 1/00; C12P 21/06; C07H 21/04
[52] U.S. Cl. .......... 435/69.1; 435/325; 435/419; 435/252.3; 435/254.2; 536/23.5; 530/350; 530/333; 530/351; 530/381; 935/9; 935/49
[58] Field of Search ............ 536/23.5; 530/350, 530/333, 351, 381; 935/9, 49; 435/69.1, 325, 419, 252.3, 254.2

[56] References Cited

FOREIGN PATENT DOCUMENTS 0315254 5/1989 European Pat. Off. .
0319944 6/1989 European Pat. Off. .

OTHER PUBLICATIONS

Biochem. Biophys. Res. Commun., 174, 586–592 (1991).
John S. Kizer et al.
Von Heijne, G., in Nucleic Acids Res. 14, 4683 (1986).
Hinnen et al., Proc. Natl. Acad. Sci. USA, 75, 1929 (1978).
Inagnostopoulos et al., J. Bacteriol. 81, 741 (1961).
M. Mandel et al., J. Mol. Biol. 53, 159 (1970).
Van Daijnkoven, et al., J. Immunol. Methods, 142, 187–198 (1991).
Martens, FEBS Letts., 234, 160–164 (1988).
Haendler, et al., Gene 83, 39–46 (1989).
Rothblatt et al., EMBO J., 6, 3455–3463 (1982).
Klebe et al., Gene 25, 333–341 (1983).
Barr et al., J. Biol. Chem. 263, 16471–16478 (1988).
Steube, K. et al., Eur. J. Biochem., 198, 651–657 (1991).
Belt et al., Gene 84, 407–417 (1989).
Ayoubi et al., Cell Tissue Res. 264, 329–334 (1991).
Gatenby et al., Trends in Biotechnology 8, 354–358 (1990).

Primary Examiner—Keith D. Hendricks
Attorney, Agent, or Firm—Henry P. Nowak

[57] ABSTRACT

The invention lies in the field of genetic engineering and, in particular, is concerned with the use of 7B2 as chaperone in vivo or in vitro. The invention accordingly concerns a method for producing a desired protein in vivo with the aid of recombinant cells capable of expressing 7B2 and of expressing and secreting said desired protein. Another aspect is accordingly an in vitro method for the deaggregation or prevention of aggregation of protein by treating the protein with 7B2.

19 Claims, 2 Drawing Sheets

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
ATGAATTCAT GCTATCTGGC CTACTG                                    26
```

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
TAGCATGCTT ACTCTGGATC CTTATC                                    26
```

( 2 ) INFORMATION FOR SEQ ID NO:3:

( i ) SEQUENCE CHARACTERISTICS:
        ( A ) LENGTH: 54 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..54

( x i ) SEQUENCE DESCRIPTION: SEQ ID NO:3:

```
ATG  CTA  TCT  GGC  CTA  CTG  TTT  TGG  CTG  GCA  TCT  GGA  TGG  ACT  CCA  GCA    48
Met  Leu  Ser  Gly  Leu  Leu  Phe  Trp  Leu  Ala  Ser  Gly  Trp  Thr  Pro  Ala
 1                 5                      10                      15

TTT  GCT                                                                          54
Phe  Ala
```

( 2 ) INFORMATION FOR SEQ ID NO:4:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Leu  Ser  Gly  Leu  Leu  Phe  Trp  Leu  Ala  Ser  Gly  Trp  Thr  Pro  Ala
 1                 5                      10                      15

Phe  Ala
```

( 2 ) INFORMATION FOR SEQ ID NO:5:

(  i  ) SEQUENCE CHARACTERISTICS:
     ( A ) LENGTH: 558 base pairs
     ( B ) TYPE: nucleic acid
     ( C ) STRANDEDNESS: double
     ( D ) TOPOLOGY: linear (  i i  ) MOLECULE TYPE: DNA (genomic)

(  i x  ) FEATURE:
     ( A ) NAME/KEY: CDS
     ( B ) LOCATION: 1..558

(  x i  ) SEQUENCE DESCRIPTION: SEQ ID NO:5:

| TAC | AGC | CCC | CGG | ACC | CCT | GAC | CGG | GTC | TCA | GAA | GCA | GAT | ATC | CAG | AGG | 48 |
| Tyr | Ser | Pro | Arg | Thr | Pro | Asp | Arg | Val | Ser | Glu | Ala | Asp | Ile | Gln | Arg | |
| | 20 | | | | 25 | | | | | 30 | | | | | | |
| CTG | CTT | CAT | GGT | GTT | ATG | GAG | CAA | TTG | GGC | ATT | GCC | AGG | CCC | CGA | GTG | 96 |
| Leu | Leu | His | Gly | Val | Met | Glu | Gln | Leu | Gly | Ile | Ala | Arg | Pro | Arg | Val | |
| 35 | | | | | 40 | | | | 45 | | | | | | 50 | |
| GAA | TAT | CCA | GCT | CAC | CAG | GCC | ATG | AAT | CTT | GTG | GGC | CCC | CAG | AGC | ATT | 144 |
| Glu | Tyr | Pro | Ala | His | Gln | Ala | Met | Asn | Leu | Val | Gly | Pro | Gln | Ser | Ile | |
| | | | | 55 | | | | | 60 | | | | | 65 | | |
| GAA | GGT | GGA | GCT | CAT | GAA | GGA | CTT | CAG | CAT | TTG | GGT | CCT | TTT | GGC | AAC | 192 |
| Glu | Gly | Gly | Ala | His | Glu | Gly | Leu | Gln | His | Leu | Gly | Pro | Phe | Gly | Asn | |
| | | | 70 | | | | | 75 | | | | | 80 | | | |
| ATC | CCC | AAC | ATC | GTG | GCA | GAG | TTG | ACT | GGA | GAC | AAC | ATT | CCT | AAG | GAC | 240 |
| Ile | Pro | Asn | Ile | Val | Ala | Glu | Leu | Thr | Gly | Asp | Asn | Ile | Pro | Lys | Asp | |
| | | 85 | | | | | 90 | | | | | 95 | | | | |
| TTT | AGT | GAG | GAT | CAG | GGG | TAC | CCA | GAC | CCT | CCA | AAT | CCC | TGT | CCT | GTT | 288 |
| Phe | Ser | Glu | Asp | Gln | Gly | Tyr | Pro | Asp | Pro | Pro | Asn | Pro | Cys | Pro | Val | |
| | 100 | | | | | 105 | | | | | 110 | | | | | |
| GGA | AAA | ACA | GAT | GAT | GGA | TGT | CTA | GAA | AAC | ACC | CCT | GAC | ACT | GCA | GAG | 336 |
| Gly | Lys | Thr | Asp | Asp | Gly | Cys | Leu | Glu | Asn | Thr | Pro | Asp | Thr | Ala | Glu | |
| 115 | | | | | 120 | | | | | 125 | | | | | 130 | |
| TTC | AGT | CGA | GAG | TTC | CAG | TTG | CAC | CAG | CAT | CTC | TTT | GAT | CCG | GAA | CAT | 384 |
| Phe | Ser | Arg | Glu | Phe | Gln | Leu | His | Gln | His | Leu | Phe | Asp | Pro | Glu | His | |
| | | | | 135 | | | | | 140 | | | | | 145 | | |
| GAC | TAT | CCA | GGC | TTG | GGC | AAG | TGG | AAC | AAG | AAA | CTC | CTT | TAC | GAG | AAG | 432 |
| Asp | Tyr | Pro | Gly | Leu | Gly | Lys | Trp | Asn | Lys | Lys | Leu | Leu | Tyr | Glu | Lys | |
| | | | 150 | | | | | 155 | | | | | 160 | | | |
| ATG | AAG | GGA | GGA | GAG | AGA | CGA | AAG | CGG | AGG | AGT | GTC | AAT | CCA | TAT | CTA | 480 |
| Met | Lys | Gly | Gly | Glu | Arg | Arg | Lys | Arg | Arg | Ser | Val | Asn | Pro | Tyr | Leu | |
| | | 165 | | | | | 170 | | | | | 175 | | | | |
| CAA | GGA | CAG | AGA | CTG | GAT | AAT | GTT | GTT | GCA | AAG | AAG | TCT | GTC | CCC | CAT | 528 |
| Gln | Gly | Gln | Arg | Leu | Asp | Asn | Val | Val | Ala | Lys | Lys | Ser | Val | Pro | His | |
| | 180 | | | | | 185 | | | | | 190 | | | | | |
| TTT | TCA | GAT | GAG | GAT | AAG | GAT | CCA | GAG | TAA | | | | | | | 558 |
| Phe | Ser | Asp | Glu | Asp | Lys | Asp | Pro | Glu | * | | | | | | | |
| 195 | | | | | 200 | | | | | | | | | | | |

( 2 ) INFORMATION FOR SEQ ID NO:6:

(  i  ) SEQUENCE CHARACTERISTICS:
          ( A ) LENGTH: 185 amino acids
          ( B ) TYPE: amino acid
          ( D ) TOPOLOGY: linear (  i i  ) MOLECULE TYPE: protein (  x i  ) SEQUENCE DESCRIPTION: SEQ ID NO:6:

| Tyr | Ser | Pro | Arg | Thr | Pro | Asp | Arg | Val | Ser | Glu | Ala | Asp | Ile | Gln | Arg |
| 1 | | | | 5 | | | | | 10 | | | | | 15 | |
| Leu | Leu | His | Gly | Val | Met | Glu | Gln | Leu | Gly | Ile | Ala | Arg | Pro | Arg | Val |
| | | | | 20 | | | | | 25 | | | | | 30 | |

| Glu | Tyr | Pro | Ala | His | Gln | Ala | Met | Asn | Leu | Val | Gly | Pro | Gln | Ser | Ile |
|---|---|---|---|---|---|---|---|---|---|---|---|---|---|---|---|
| | | 35 | | | | | 40 | | | | | 45 | | | |

| Glu | Gly | Gly | Ala | His | Gly | Leu | Gln | His | Leu | Gly | Pro | Phe | Ala | Asn |
|---|---|---|---|---|---|---|---|---|---|---|---|---|---|---|
| | 50 | | | | | 55 | | | | | 60 | | | |

| Ile | Pro | Asn | Ile | Val | Ala | Glu | Leu | Thr | Gly | Asp | Asn | Ile | Pro | Lys | Asp |
|---|---|---|---|---|---|---|---|---|---|---|---|---|---|---|---|
| 65 | | | | | 70 | | | | 75 | | | | | | 80 |

| Phe | Ser | Glu | Asp | Gln | Gly | Tyr | Pro | Asp | Pro | Pro | Asn | Pro | Cys | Pro | Val |
|---|---|---|---|---|---|---|---|---|---|---|---|---|---|---|---|
| | | | | 85 | | | | | 90 | | | | | 95 | |

| Gly | Lys | Thr | Asp | Asp | Gly | Cys | Leu | Glu | Asn | Thr | Pro | Asp | Thr | Ala | Glu |
|---|---|---|---|---|---|---|---|---|---|---|---|---|---|---|---|
| | | | 100 | | | | | 105 | | | | | 110 | | |

| Phe | Ser | Arg | Glu | Phe | Gln | Leu | His | Gln | His | Leu | Phe | Asp | Pro | Glu | His |
|---|---|---|---|---|---|---|---|---|---|---|---|---|---|---|---|
| | | 115 | | | | | 120 | | | | | 125 | | | |

| Asp | Tyr | Pro | Gly | Leu | Gly | Lys | Trp | Asn | Lys | Lys | Leu | Leu | Tyr | Glu | Lys |
|---|---|---|---|---|---|---|---|---|---|---|---|---|---|---|---|
| | 130 | | | | | 135 | | | | | 140 | | | | |

| Met | Lys | Gly | Gly | Glu | Arg | Arg | Lys | Arg | Arg | Ser | Val | Asn | Pro | Tyr | Leu |
|---|---|---|---|---|---|---|---|---|---|---|---|---|---|---|---|
| 145 | | | | | 150 | | | | | 155 | | | | | 160 |

| Gln | Gly | Gln | Arg | Leu | Asp | Asn | Val | Val | Ala | Lys | Lys | Ser | Val | Pro | His |
|---|---|---|---|---|---|---|---|---|---|---|---|---|---|---|---|
| | | | | 165 | | | | 170 | | | | | | 175 | |

| Phe | Ser | Asp | Glu | Asp | Lys | Asp | Pro | Glu |
|---|---|---|---|---|---|---|---|---|
| | | | 180 | | | | | 185 |

( 2 ) INFORMATION FOR SEQ ID NO:7:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

TAGCATGCTT AGTTCCACTT GCCCAAGCC    29

( 2 ) INFORMATION FOR SEQ ID NO:8:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

ATAAGCTTTT ACTCTCCTCC CTTCATCTT    29

( 2 ) INFORMATION FOR SEQ ID NO:9:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

ATAAGCTTTT ATGCAACAAC ATTATCCAG    29

( 2 ) INFORMATION FOR SEQ ID NO:10:

( i ) SEQUENCE CHARACTERISTICS:

( A ) LENGTH: 69 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 7..63

( x i ) SEQUENCE DESCRIPTION: SEQ ID NO:10:

```
GAATTC ATG CTT TTG CAA GCT TTC CTT TTC CTT TTG GCT GGT TTT GCA        48
       Met Leu Leu Gln Ala Phe Leu Phe Leu Leu Ala Gly Phe Ala
                       5               10

GCC AAA ATA TCT GCA CTCGAG                                            69
Ala Lys Ile Ser Ala
 15
```

( 2 ) INFORMATION FOR SEQ ID NO:11:

( i ) SEQUENCE CHARACTERISTICS:
( A ) LENGTH: 19 amino acids
( B ) TYPE: amino acid
( D ) TOPOLOGY: linear ( i i ) MOLECULE TYPE: protein ( x i ) SEQUENCE DESCRIPTION: SEQ ID NO:11:

```
Met Leu Leu Gln Ala Phe Leu Phe Leu Leu Ala Gly Phe Ala Ala Lys
 1               5                   10                  15

Ile Ser Ala
```

( 2 ) INFORMATION FOR SEQ ID NO:12:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..36

( x i ) SEQUENCE DESCRIPTION: SEQ ID NO:12:

```
GCA GCC AAA ATA TCT GCA TAC AGC CCC CGG ACC CCT                       36
Ala Ala Lys Ile Ser Ala Tyr Ser Pro Arg Thr Pro
             5                   10
```

( 2 ) INFORMATION FOR SEQ ID NO:13:

( i ) SEQUENCE CHARACTERISTICS:
( A ) LENGTH: 12 amino acids
( B ) TYPE: amino acid
( D ) TOPOLOGY: linear ( i i ) MOLECULE TYPE: protein ( x i ) SEQUENCE DESCRIPTION: SEQ ID NO:13:

```
Ala Ala Lys Ile Ser Ala Tyr Ser Pro Arg Thr Pro
 1               5                   10
```

( 2 ) INFORMATION FOR SEQ ID NO:14:

( i ) SEQUENCE CHARACTERISTICS:
( A ) LENGTH: 20 base pairs
( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

ATGAGCTCCA CCTTCAATGC 20

( 2 ) INFORMATION FOR SEQ ID NO:15:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 9..20

( x i ) SEQUENCE DESCRIPTION: SEQ ID NO:15:

TAGAATTC ATG CTT TTG CAA G 21
         Met Leu Leu Gln ( 2 ) INFORMATION FOR SEQ ID NO:16:

( i ) SEQUENCE CHARACTERISTICS:
( A ) LENGTH: 4 amino acids
( B ) TYPE: amino acid
( D ) TOPOLOGY: linear ( i i ) MOLECULE TYPE: protein ( x i ) SEQUENCE DESCRIPTION: SEQ ID NO:16:

Met Leu Leu Gln
 1

( 2 ) INFORMATION FOR SEQ ID NO:17:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

ATATGGATCC TCTAGAACCT TTCATCATCT 30

( 2 ) INFORMATION FOR SEQ ID NO:18:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

TAATGAATTC GGTAGTATTA GCGGTTGAGT 30

RECOMBINANT PRODUCTION OF PROTEINS USING 7B2 PROTEIN

This is a Divisional of Ser. No. 08/244,492, filed Sep. 2, 1994, now U.S. Pat. No. 5,708,140.

The invention lies in the field of genetic engineering and, in particular, is concerned with the use of 7B2 as chaperone in vivo or in vitro. The invention accordingly concerns a method for producing a desired protein in vivo with the aid of recombinant cells capable of expressing 7B2 and of expressing and secreting said desired protein. Another aspect is accordingly an in vitro method for the deaggregation or prevention of aggregation of protein by treating the protein with 7B2.

BACKGROUND OF THE INVENTION

Different transport mechanisms for secretory proteins exist within the eukaryotic cell. All secretory cells are capable of releasing secretory proteins by protein synthesis at the endoplasmatic reticulum (ER), transport via ER to the Golgi apparatus and from the Golgi apparatus to so-called transport granules. The membrane of a transport granule fuses with the plasma membrane after which the secretory proteins can leave the cell by exocytosis. When secretory proteins are made they are also released, in other words there is no regulation of protein release. This protein transport is subsequently designated the constitutive secretory route and is present in all eukaryotic cells including yeast. Prokaryotic cells also have a not regulated, i.e. constitutive, route of protein secretion.

The release of certain secretory proteins is known to be regulated in a restricted group of higher eukaryotic cells. These cells comprise neurons and endocrine cells, in other words cells producing precursors of bioactive proteins. The synthesis in these cells takes place at the ER, transport goes from ER to Golgi as in the constitutive cells but then proceeds from Golgi to secretory granules. In these secretory granules the correct environment is present for the specific post-translational modifications of the precursors. This type of protein transport is indicated as the regulated route. The exocytosis of the bioactive proteins only occurs when the cell undergoes a correct external stimulus. This type of cell is indicated as a regulated secretory cell.

Correct folding of proteins produced by a cell is ensured by molecular chaperone proteins which are essential for correct functioning of cells as they ensure that proteins produced by the cells are folded in a correct manner. Correct folding is necessary for correct transport of these proteins to the right destination within the cell. Thus, chaperones are not only necessary for correct protein folding but also for correct protein transport. Specific chaperone proteins have e.g. been described for protein transport from the cell cytoplasm to cell organelles such as the mitochondrion, the chloroplast, the cell nucleus and the ER. The production of many of these proteins is induced in cells that are subjected to a heat shock and chaperone proteins are therefore often called "heat-shock proteins".

The production of recombinant bioactive protein has become possible through developments in the field of recombinant DNA technology, but is often not successful in practice because frequently folding and/or secretion of the heterologous proteins that are to be produced does not occur correctly or occurs inefficiently. Such a problem usually occurs in cases of strong expression of the heterologous protein in a cell which has insufficient capacity to ensure correct folding and optionally secretion of a protein that is produced in a large amount. The problem arises from the fact that recombinant proteins are produced in large amounts in prokaryotic cells or eukaryotic cells that so that the activity of the cellular folding proteins is not sufficient for folding the huge amount of foreign protein. Additional problems arise if recombinant proteins are desired to be processed and secreted but the host cells comprise only to an insufficient extent a route of protein transport. Moreover, if proproteins such as prohormones or precursors of neuropeptides are intended to be produced in higher eukaryotic cells which proproteins are desired to be processed in the cell to bioactive proteins, problems arise if cells are used which comprised no regulated secretory route or comprise such route only to an insufficient extend. These proteins will therefore not undergo the correct post-translational modifications required to function as a completely biologically active protein. This is in particular the case for recombinant proteins that are in nature produced and released through regulated protein transport.

Another problem is that proteins often tend to aggregate in solution. The formation of aggregates then causes loss in the activity of biologically active proteins or prevents the correct folding of unfolded or malfolded proteins by in vitro refolding methods.

OBJECT OF THE INVENTION

The present invention offers a solution to such problems in that methods are provided for the use of 7B2 as a chaperone in vitro or in vivo. The use of 7B2 as chaperone allows an efficient production of proteins in a transformed host cell by co-expression of 7B2 with the desired protein such that the latter can be treated by the host cell in vivo, or by treating protein with 7B2 in vitro.

7B2 is in nature exclusively present and active in regulated cells such as neurons and endocrine cells. In the prior art 7B2 is described as a possible GTP-binding protein that like many other small GTP-binding proteins could be involved in the fusion of two organelle membranes within the cell or the fusion of an organelle membrane with the cell membrane.

The present invention is now based on the surprising fact that 7B2 has a chaperone function which can be used in vitro or in vivo, in particular in vitro for deaggregation and prevention of aggregation of protein, preferably monomeric protein, and in vivo for the efficient production of recombinant protein from a host cell if 7B2 and the recombinant protein are co-expressed in the cell.

SUMMARY OF THE INVENTION

The present invention concerns a method for the preparation of a protein, characterized in that the protein is treated with 7B2 in vivo or in vitro. Thus, the present invention includes a method for the preparation of a protein by means of a host cell, preferably a eukaryotic host cell, transformed with genetic information encoding a polypeptide having the amino acid sequence of a bioactive protein or a precursor thereof and capable of expressing this polypeptide or precursor, characterized in that such cell is additionally transformed with genetic information which enables the cell to co-express 7B2 with the said polypeptide or precursor and that the polypeptide or precursor is treated in vivo in such a manner that the deaggregation or correct folding of the polypeptide or precursor is supported or that the polypeptide or precursor, optionally after the cell has been stimulated to release, is secreted in higher amounts than if 7B2 is absent.

A preferred embodiment of the invention is a method in which a eukaryotic host cell is used which has a regulated route of protein secretion, even more preferred is the use of a neuronal or endocrine cell. Preferred is also a method in which the polypeptide or precursor is treated in vivo in such manner that the polypeptide, optionally after the cell has been stimulated to release, is secreted, in an even more preferred embodiment the secreted polypeptide is a bioactive protein.

Another preferred embodiment is a method in which a yeast cell is used as host. More preferably, the yeast cell is transformed with a DNA sequence capable of expressing a polypeptide having the amino acid sequence of a bioactive protein, which polypeptide in an even more preferred embodiment is secreted. In a most preferred embodiment the secreted polypeptide has the amino acid sequence of IGF-1.

A method of the present invention can be used for the preparation of a polypeptide having the amino acid sequence of a bioactive protein selected from the group of peptide hormones, neuropeptides, growth factors and coagulation factors, preferentially a peptide hormone or a neuropeptide.

The meaning of 7B2 is given hereinafter. In a most preferred embodiment 7B2 is of human origin.

The invention also concerns a transformed host cell which can be used in the present invention. Accordingly, the invention concerns a transformed host cell, preferentially a eukaryotic host cell, transformed with genetic information encoding a polypeptide having the amino acid sequence of a bioactive protein or a precursor thereof and capable of expressing this polypeptide or precursor, characterized in that such cell is additionally transformed with genetic information which enables the cell to co-express 7B2 with the said polypeptide or precursor and treating the polypeptide or precursor in vivo in such a manner that the correct folding of the polypeptide or precursor is supported and/or, optionally after the cell has been stimulated to release, the polypeptide or precursor is secreted in higher amounts than if 7B2 is absent.

A preferred host cell is a transformed eukaryotic cell which has a regulated route of protein secretion, more preferred is a neuronal or endocrine cell. A preferred host cell is also a transformed yeast cell.

A transformed cell of the invention is preferentially characterized in that it is transformed with genetic information enabling it to express human 7B2.

A transformed cell of the invention is also preferentially characterized in that it is transformed with DNA encoding a bioactive protein selected from the group of peptide hormones, neuropeptides, growth factors and coagulation facors, more preferentially with DNA encoding a peptide hormone or a neuropeptide, or with a DNA encoding a precursor of such a bioactive protein.

A transformed cell of the invention, in particular a transformed yeast cell, is most preferentially characterized in that it is transformed with DNA encoding IGF-1.

The invention also concerns preferentially a method for the deaggregation or prevention of aggregation of protein in vitro, characterized in that the protein or aggregates thereof are treated with 7B2.

The invention also concerns a method for the preparation of 7B2 in a transformed cell, preferenttially in a E. coli or yeast cell.

DETAILED DESCRIPTION OF THE INVENTION

The present invention concerns a method for the preparation of a protein, characterized in that the protein is treated with 7B2 in vivo in vitro. In particular, the present invention concerns (a) a method for the improvement of the production of recombinant protein in vivo, and (b) a method for the deaggregation or for the prevention of the aggregation of protein, preferably monomeric protein, by using 7B2 in vitro.

7B2 is present in the regulated secretory route of regulated cells such as neurons and endocrine cells and is therefore presumed to have specific interaction with precursors of bioactive proteins produced by such cells, such as neuropeptides or peptide hormones. It is characteristic for the production of precursors of secreted bioactive proteins such as neuropeptides or peptide hormones that they are in the cell separated from the other (constitutive) secretory proteins and follow a route finally leading to the regulated granules. 7B2 is required for this separation mechanism and it appears that 7B2 is a chaperone protein belonging to the group of chaperonins responsible for the correct transport of secretory proteins from the ER via the Golgi apparatus to the secretory granules of cells and that 7B2 is necessary for correct functioning of the regulated route of protein transport within regulated cells such as neuronal or endocrine cells. 7B2 specifically binds precursors of bioactive proteins and carries them to the regulated route of protein transport. Such a chaperone has not yet been described. Moreover, 7B2 is the only protein with chaperone function that is a secretory protein (that can therefore leave the cell).

The first aspect of the present invention is therefore based on the new and surprising finding that the known 7B2 belongs to the molecular chaperone proteins and apparently fulfills a role in transporting certain secretory proteins from the ER via the Golgi apparatus to the secretory granules of cells. Following the correct route is especially of large importance for precursors of bioactive proteins as they must arrive at the correct microenvironment within the cell (viz. in the secretory granules of the regulated route) to undergo the specific post-translational modifications in the correct manner. Another aspect of the invention is that the chaperone function of 7B2 can not only be used for the improved production of protein in a cell having a regulated secretory route. Proteins which are substrate of 7B2 can also be easier produced in a prokaryotic or eukaryotic cell having no regulated secretory route because 7B2 supports the deaggregation and folding of the said proteins. Thus, 7B2 co-expression improves the production of intracellular protein as well as of protein secreted via the constitutive or regulated route. The 7B2 chaperone function may in a further aspect of the invention also be used in vitro for supporting correct folding and, preferably, for deaggregation or prevention of aggregation of protein.

For use in vivo a DNA encoding 7B2 is coexpressed in a host cell with a gene encoding the desired protein. A suitable host cells is, for example, a prokaryotic cell such as E. coli or a eukaryotic cell, preferably a yeast cell or preferably a cell having a regulated route for protein secretion, for example a neuronal or endocrine cell. Co-expression of 7B2 with the desired protein is in particular advantageous because 7B2 helps to prevent or alleviate folding problems in overproducing cells; in other words in cases where the cell itself does not have sufficient capacity to fold the (over) produced protein in the correct manner, for example in a prokaryotic cell such as E. coli, or preferentially in a yeast cell or more preferentially in the case of a cell having a regulated secretory route for correct transport to the regulated granules.

Proteins which can be made subject of 7B2 function in vivo or in vitro are defined hereinafter.

Substrated for the 7B2 function of the invention are proteins that are dependent also in nature on 7B2 for correct transport are the precursors of bioactive proteins such as peptide hormones and neuropeptides, in other words proteins that are transported and leave the cell via the regulated route of protein transport that occurs in nerve cells and endocrine cells. Suitable substrates for 7B2 in vivo or in vitro action are further presumably proteins with an aliphatic α-helix, for example such having between about 10 and about 15 amino acids. In cases where the motif is not cleaved off during processing of teh precursor and thus is present in the final product, i.e. the bioactive protein, this protein itself is suitable as substrate for 7B2. Suitable substrates for 7B2 in vivo or in vitro action are also proteins which tend to aggregate in solution.

It is probable that precursors of bioactive proteins such as neuropeptides or peptide hormones have specific domains within their structure that are recognized by 7B2 and are involved with the interaction. A consensus sequence was found within the structure of prohormones [i.e. large proteins that can be split into biologically active proteins in the secretory granules of the cell, e.g. proopiomelanocortin (POMC) which can be split into various bioactive proteins such as the adrenocorticotropic hormone (ACTH), the opiate-like peptide β-endorphin and the melanophore-stimulating hormone (MSH)] that could serve as signal for the selection of secretory proteins to the regulated release route and for the interaction with 7B2 ("A motif found in proproteins and prohormones that may target them to secretory vesicles", Biochem. Biophys, Res. Commun. 174, 586–592, 1991).

"Precursors" in context with the present invention means proproteins which can be cleaved to biologically active proteins, for example the prohormone POMC.

The new finding that 7B2 acts as chaperone can be used when folding and/or secretion of proteins is incorrect or takes place inefficiently upon production of heterologous proteins in a recombinant host. The co-expression of 7B2 leads to a decrease in the in vivo folding problems of 7B2 substrate proteins in a prokaryotic as well as in a eukaryotic cell Preferred is the in vivo application of 7B2 in a eukaryotic cell In particular, coexpression of a 7B2 gene and a gene encoding a bioactive protein or a precursor thereof in a yeast cell or of a 7B2 gene and a gene encoding a precursor of a bioactive protein in a eukaryotic cell with regulated protein transport.

As far as the expression in a higher eukaryotic cell is concerned, the desired final products, i.e. bioactive proteins, are preferably prepared by producing and processing the natural precursor in the cell. Thus, in a preferred embodiment of the invention a precursor is produced and correctly processed in a recombinant higher eukaryotic cell wherein the co-expression of 7B2 with the precursor of the bioactive protein ensures that the protein follows the regulated secretory route. In another preferred embodiment a yeast cell is used and the methods for producing bioactive protein include either the production of precursors which can be processed in vitro or the direct production of a protein having the amino acid sequence of a desired bioactive protein, which optionally may be refolded in vitro to yield the bioactive form.

The following are examples of genes the products of which can be used as substrates of 7B2 in the present invention:

Products of the members of the neuropeptide gene families, for example of the opioid gene family, in particular of the enkephalin gene, the dynorphin gene or the pro-opiomelanocortin gene, of the posterior pitiutary family, in particular of the vasopressin gene or the oxytocin gene, of the cck/gastrin family, in particular of the gastrin gene or the cholecystokinin gene, of the somatostatin gene family, in particular of the somatostatin gene, the neuropeptide Y gene, the peptide YY gene or pancreatic polypeptide gene, of the calcitonin gene family, in particular of the calcitonin I gene, the calcitonin II gene or the islet amyloid polypeptide gene, of the natriuretic factor gene family, in particular of the atrial natriuretic factor gene, the brain natriuretic factor gene or the C-type natriuretic factor gene, of the bombesin gene family, in particular of the gastrin releasing peptide gene or the neuromedin B gene, of the endothelin gene family, in particular of the endothelin 1, 2 or 3 gene, of the secretin gene family, in particular of the secretin gene, the glucagon gene, the vasoactive intestinal peptide gene, the gastric inhibitory peptide gene, the growth hormone releasing factor gene or the pituitary adenylate cyclase activating peptide gene, of the kinin gene family, in particular of the tachykinin A or B gene, the K-kininogen gene, the neurotensin gene or the angiotensinogen gene. Products of other genes which can be prepared according to the present invention are the products of the members od the insulin-like gene family, in particular of the IGF-1 gene, the IGF-2 gene, the relaxin gene or the insulin gene, or of various other genes, in particular of the motilin gene, the galanin gene, the corticotropin releasing factor gene, the thyrotropin releasing factor gene, the gonadotropin releasing factor gene or the melanin concentrating hormone gene. Preferred products are those of the members of the insulin-like gene family, preferably IGF-1 or IGF-2, more preferably IGF-1. Preferred are also the products of the prolactin gene and of the POMC gene, more preferably prolactin and ACTH respectively. The present invention may also be used for the production of growth factors (e.g. TGF, NGF, and the like), coagulation factors and other blood proteins (e.g. factor VIII, tPA, van Willebrands factor and the like).

Higher eukaryotic cells in connection with the present invention are animal or plant cells, preferably animal cells, more preferably cells having a regulated route of protein transport, even more preferably endocrine or neuronal cells including cell lines derived from endocrine or neuronal tumour cells.

The term 7B2 used in connection with the present invention most preferably means human 7B2 as described in European patent application EP-A 0 315 254. However, the term 7B2 is not limited to the human molecule but includes also corresponding proteins from different organisms. Apart from human 7B2 the structures of mouse, rat, cow, salmon and clawed frog *Xenopus laevis* 7B2 proteins have been described and can be used in the present invention. Other corresponding 7B2 proteins can be identified by a comparison of the amino acid sequence with the sequences of the known 7B2 proteins because specifically the $NH_2$-terminal portion of 7B2 is strongly conserved and because all 7B2 proteins contain further conserved sequences showing similarity in all species. The term 7B2 is also intended to include derivatives of naturally occurring 7B2 proteins which derivatives have 7B2 activity. Such derivatives can be fusion proteins, conjugates and, in particular, fragments, for example such corresponding to the first 137, 149 or 170 amino acids of human 7B2, more preferably the said human fragments.

It is surprising that 7B2 functions not only in cells having a regulated pathway for the processing and secretion of proteins but also in the preparation of heterologous proteins in prokaryotic cells and other eukaryotic cells, such as higher eukaryotic cells having no regulated secretory route or fungal cells, especially yeast cells. Products of genes encoding a precursor or even of genes encoding protein sequences as they occur during the processing of a precursor of a bioactive protein in nature, i.e. intermediate or final products of the precursors in the naturally occurring secretion pathways, can be produced in higher amounts in such cells if they are co-expressed with 7B2. The advantageous effect on correct folding is useful for the production of intracellularly stored protein, in particular if prokaryotic cells, for example E. coli, are used. Of even more advantage, however, is the use of 7B2 for the production of secreted proteins, i.e. proteins which are produced in the cell as preproteins having a signal sequence. In the context of the present invention it is understood that all proteins which are inteded to be secreted are produced in functional linkage with a signal sequence which is cleaved off in the cell. However, the term "Precursor" in context with the present invention is not used in the sense of "protein having a signal sequence" (i.e. pre-proteins) but means pro-proteins which can be processed to biologically active proteins, for example the prohormone POMC. These pro-proteins may after translation of the mRNA also be linked to a signal sequence if the natural processing product or the pro-protein itself is intended to be secreted. If a secreted product is intended to be produced, 7B2 also needs a signal sequence in order to be transported the same way as the substrate protein.

The present invention accordingly concerns a method for the preparation of a protein, characterized in that the protein is treated with 7B2 in vivo or in vitro. Thus, the present invention includes a method for the preparation of a protein by means of a host cell, preferably a eukaryotic host cell transformed with genetic information encoding a polypeptide having the amino acid sequence of a bioactive protein or a precursor thereof and capable of expressing this polypeptide or precursor, characterized in that such cell is additionally transformed with genetic information which enables the cell to co-express 7B2 with the said polypeptide or precursor and that the polypeptide or precursor is treated in vivo in such a manner that the deaggregation or correct folding of the polypeptide or precursor is supported or that the polypeptide or precursor, optionally after the cell has been stimulated to release, is secreted in higher amounts than if 7B2 is absent.

The invention accordingly provides a method for producing a bioactive protein by means of a recombinant eukaryotic cell, preferably higher eucaryotic cell, more preferably such having a regulated route of protein secretion, that has been provided with genetic information encoding a protein having the amino acid sequence of a desired bioactive peptide or, preferably, a precursor of a bioactive protein and with genetic information encoding 7B2 and that is capable of co-expressing said protein or precursor and 7B2 and treating said protein or precursor in such a manner that the desired bioactive protein optionally after stimulation of the cell to release is secreted.

The invention also provides a recombinant eukaryotic cell, preferably higher eucaryotic cell, more preferably such having a regulated route of protein secretion, that has been provided with genetic information encoding a protein having the amino acid sequence of a desired bioactive peptide or, preferably, a precursor of a bioactive protein and with genetic information encoding 7B2 and that is capable of co-expressing said protein or precursor and 7B2 and treating said protein or precursor in such a manner that the desired bioactive protein optionally after stimulation of the cell to release is secreted It can be desirable to stimulate secretion of the bioactive protein by the cells. Which substances are used for such stimulation depends to a certain extent on the type of cell that is used for the production. A fairly generally applicable means for stimulating this secretion, in particular in the case of eukaryotic cells of the regulated type, is cAMP or a derivative thereof, such as 8-Br-cAMP.

The invention also provides a method for producing a protein having the amino acid sequence of a precursor of a bioactive protein or, preferably, of a bioactive protein itself, in a prokaryotic or euakaryotic cell, preferably in a yeast cell, that has been provided with genetic information encoding a protein having the amino acid sequence of a desired a precursor of a bioactive protein or, preferably, the bioactive protein itself and with genetic information encoding 7B2 and that is capable of co-expressing said protein or precursor and 7B2 the protein having the amino acid sequence of the bioactive petide or precursor thereof is treated in the cell such that deaggregation or correct folding is supported or, preferably and more preferably in connection with the yeast cell, such that it is secreted and can be recovered from the supernatant.

The invention also provides a recombinant a prokaryotic or euakaryotic cell, preferably in a yeast cell, that has been provided with genetic information encoding a protein having the amino acid sequence of a desired a precursor of a bioactive protein or, preferably, the bioactive protein itself and with genetic information encoding 7B2 and that is capable of co-expressing said protein or precursor and 7B2 the protein having the amino acid sequence of the bioactive petide or precursor thereof is treated in the cell such that deaggregation or correct folding is supported or, preferably and more preferably in connection with the yeast cell, such that it is secreted and can be recovered from the supernatant.

The method according to the invention comprising co-expression of 7B2 and the heterologous protein in a genetically manipulated eukaryotic host cell of the regulated type can be carried out in a method known per se, for example according to the method described for the plant chaperone rubisco. Likewise, the method according to the invention comprising co-expression of a 7B2 gene and a gene encoding a bioactive protein or a precursor thereof in a genetically manipulated yeast cell can be carried out in a method known per se. In both cases the cell comprises an expression cassette for the expression of 7B2 and an expression cassette for a protein defined hereinbefore which is desired to be produced. The term "expression cassette" means a DNA sequence capable of expressing a polypeptide and comprises a promoter, if desired a signal sequence, further a structural gene, if desired a transcriptional terminator and optionally a transcriptional enhancer, ribosomal binding site and/or further regulatory sequences.

Means for the construction of vectors suitable for the expression of 7B2 or the desired protein or precursor thereof are the vectors and regulatory sequences available in the art. Expression vectors can be prepared according to conventional techniques. Useful vectors and regulatory sequences are exemplified hereinafter for the expression of a 7B2 gene for the purpose of 7B2 production. However, the same vectors and regulatory sequences can also be analogously applied to the problem of co-expressing 7B2 and desired recombinant protein.

The invention also concerns the production of 7B2 per se for use in in vitro treatment of protein in order to deaggregate the protein or to prevent the aggregation thereof. 7B2 is produced by a method comprising transforming a host cell, preferably an *E. coli* cell or a yeast cell, with a hybrid vector comprising an expression cassette for the expression of 7B2.

A wide variety of promoter sequences may be employed, depending on the nature of the host cell. Examples for promoters are $\lambda P_L$, $\lambda P_R$, *E. coli* lac, trp, tac, yeast TRP1-, ADHI-, ADHII-, PHO3-, PHO5-, or glycolytic promoters such as the promoter of the enolase, glyceraldehyde-3-phosphate dehydrogenase, 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, or promoters derived from eukaryotic viruses, e.g. SV40, Rous sarcoma virus, adenovirus 2, bovine papilloma virus, papovavirus, cytomegalovirus derived promoters or mammalian cell derived promoters, e.g. of the actin, collagen, myosin, or β-globin gene. The eukaryotic promoters may be combined with enhancing sequences such as the yeast upstream activating sequences (UAS) or viral or cellular enhancers such as the cytomegalovirus IE enhancers, SV40 enhancer, immunoglobulin gene enhancer or others.

Enhancers are transcription-stimulating DNA sequences, e.g. derived from viruses such as Simian virus, polyoma virus, bovine papilloma virus or Moloney sarcoma virus, or of genomic origin. An enhancer sequence may also be derived from the extrachromosomal ribosomal DNA of *Physarum polycephalum* (PCT/EP 8500278), or it may be the upstream activation site from the acid phosphatase PHO5 gene (EP Appl. No. 86 111 820.6), or the PHO5, trp, PH05-GAPDH hybrid (EP Appl. No. 86 111 820.6), or the like promoter.

Signal sequences may be, for example, a presequence or secretory leader directing the secretion of the polypeptide, or the like. A signal sequence suitable for the secretion in a yeast cell is, for example, the SUC2 signal sequence or the signal sequence of the yeast α-factor. Further signal sequences are known from literature, e.g. those compiled by von Heijne, G., Nucleic Acids Res. 14, 4683 (1986).

In a preferred embodiment of the invention a 7B2 gene is functionally linked with a signal sequence which is functional in yeast, for example the SUC2 signal sequence or with the homologous 7B2 signal sequence. It is also preferred to use a constitutive yeast promoter. The 7B2 expression cassette is linked to a yeast vector and a yeast cell is transformed with the vector. 7B2 is secreted to the supernatant and may be isolated, if desired, according to conventional methods.

In another preferred embodiment of the invention a 7B2 gene or, more preferably a fusion gene containing the 7B2 coding sequence linked to a heterologous protein, preferentially an *E. coli* protein, more preferentially a protein supporting the isolation of 7B2, for example by having an affinity to a ligand which can be used for affinity chromatography, is expressed in a prokaryotic cell, preferentially *E. coli*, under the control of a promoter functional in the said cell and 7B2 is recovered from the cell. It is preferred to cut the fusion protein with an enzyme such that 7B2 is liberated from the fusion protein.

The invention also concerns a hybrid vector for the expression of 7B2 in a yeast or prokaryotic cell, said hybrid vector comprising an expression cassette for the expression of a 7B2 gene.

Hybrid vectors which can be used in the present invention may be derived from any vector useful in the art of genetic engineering, such as from viruses, phages, cosmids, plasmids or chromosomal DNA, such as derivatives of SV40, Herpes-viruses, Papilloma viruses, Retroviruses, Baculovirus, phage λ, e.g. NM 989 or EMBL4, or phage M13, e.g. M13mp8 phage DNA (ref. 15) linearized by BamHI digestion, bacterial plasmids, e.g. pBR322, pUC18, or yeast plasmids, e.g. yeast 2 µ plasmid, or a defective virus, phage or plasmid in the presence of a helper virus, phage or plasmid allowing replication of said defective virus, phage or plasmid, e.g. M13(+)KS vector in presence of e.g. M14K07 helper phage.

The hybrid vectors of the invention provide for replication and optionally expression of a desired DNA in a suitable host, either as an extrachromosomal element or by integration in the host chromosome. Several possible vector systems are available for integration and expression of the cloned DNA of the invention. In principle, all vectors which replicate or replicate and express a desired polypeptide gene comprised in an expression cassette of the invention in the chosen host are suitable. The vector is selected depending on the host cell envisaged for transformation. In principle, the hybrid vectors of the invention comprise the desired expression cassette as mentioned hereinbefore, an origin of replication or an autonomously replicating sequence, dominant marker sequences, optionally expression control sequences essential for the transcription and translation of the desired DNA and, optionally, for the secretion of the desired product and, optionally, additional restriction sites.

An origin of replication or an autonomously replicating sequence (a DNA element which confers autonomously replicating capabilities to extrachromosomal elements) is provided either by construction of the vector to include an exogeneous origin such as derived from Simian virus (SV 40) or another viral source, or by the host cell chromosomal mechanisms.

A hybrid vector of the invention may contain selective markers depending on the host which is to be transformed, selected and cloned. Any marker gene can be used which facilitates the selection of transformants due to the phenotypic expression of the marker. Suitable markers are particularly those expressing antibiotic resistance, e.g. against tetracycline or ampicillin, or, in the case of auxotrophic fungal mutants, genes which complement host lesions. Corresponding genes confer, for example, resistance to the antibiotic cycloheximide, or provide for prototrophy in an auxotrophic yeast mutant, for example the urs3, leu2, his3 or trp1 gene. It is also possible to employ as markers structural genes which are associated with an autonomously replicating segment providing that the host to be transformed is auxotrophic for the product expressed by the marker.

Furthermore, the invention concerns a transformed host cell for amplifying the recombinant DNA molecules of the invention or particularly for expressing an expression cassette comprised in a recombinant DNA molecule of the invention, either for the purpose of coexpressing a desired protein and 7B2 or for the purpose of producing 7B2 itself.

Examples of suitable hosts, particularly for amplifying the recombinant DNA molecules of the invention, are microorganisms which are devoid of or poor in restriction enzymes or modification enzymes, such as bacteria, in particular stains of *Escherichia coli*, for example *E. coli* X1776, *E. coli* Y1090, *E. coli* W3110, *E. coli* HB101/LM1035, *E. coli* JA 221, *E. coli* DH5α, or preferentially *E. coli* DH5α', JM109, MH1 or HB101, or *E. coli* K12 strain, *Bacillus subtilis, Bacillus stearothermophilus*, Pseudomonas, Haemophilus, Streptococcus and others, and yeasts, for example *Saccha-* romyces cerevisiae such as S. cerevisiae GRF 18. Further suitable host cells are cells of higher organisms, in particular established continuous human or animal cell lines, e.g. human embryonic lung fibroblasts L132, human malignant melanoma Bowes cells, HeLa cells, SV40 virus transformed kidney cells of African green monkey COS-7 or Chinese hamster ovary (CHO) cells. Of particular relevance for the preparation of bioactive protein by coexpressing a precursor of the bioactive protein and 7B2 are cell lines derived from neuronal or endocrine tumour cells.

The invention concerns also a method for the preparation of such transformants comprising treatment of a suitable host cell under transforming conditions with a recombinant DNA molecule of the present invention, especially a hybrid vector of the invention, optionally together with a selection marker gene and optionally selecting the transformants.

Transformation of microorganisms is carried out according to conventional methods as described in the literature, for example for S. cerevisiae (A. Hinnen et al., Proc.Natl.Acad.Sci.USA, 75, 1929,1978), for B. subtilis (Anagnostopoulos et al., J. Bacteriol. 81, 741, 1961), and for E. coli (M. Mandel et al., J. Mol. Biol. 53, 159, 1970).

Accordingly, the transformation procedure of E. coli cells includes, for example, $Ca^{2+}$ pretreatment of the cells so as to allow DNA uptake, and incubation with the hybrid vector. The subsequent selection of the transformed cells can be achieved, for example, by transferring the cells to a selective growth medium which allows separation of the transformed cells from the parent cells dependent on the nature of the marker sequence of the vector DNA. Preferably, a growth medium is used which does not allow growth of cells which do not contain the vector. The transformation of yeast comprises, for example, steps of enzymatic removal of the yeast cell wall by means of glucosidases, treatment of the obtained spheroplasts with the vector in the presence of polyethylene glycol and $Ca^{2+}$ ions, and regeneration of the cell wall by embedding the spheroplasts into agar. Preferably, the regeneration agar is prepared in a way to allow regeneration and selection of the transformed cells as described above at the same time.

Transformation of cells of higher eukaryotic origin, such as mammalian cell lines, is preferably achieved by transfection. Transfection is carried out by conventional techniques, such as calcium phosphate precipitation, microinjection, protoplast fusion, electroporation, i.e. introduction of DNA by a short electrical pulse which transiently increases the permeability of the cell membrane, or in the presence of helper compounds such as diethylaminoethyldextran, dimethyl sulfoxide, glycerol or polyethylene glycol, and the like. After the transfection procedure, transfected cells are identified and selected e.g. by cultivation in a selective medium chosen depending on the nature of the selection marker, for example standard culture media such as Dulbecco's modified Eagle medium (DMEM), minimum essential medium, RPMI 1640 medium and the like, containing e.g. the corresponding antibiotic.

The transformed host cells are cultured by methods known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/or carbonates of sodium, potassium, magnesium and calcium. The medium furthermore contains, for example, growth-promoting substances, such as trace elements, for example iron, zinc, manganese and the like.

The medium is preferably so chosen as to exert a selection pressure and prevent the growth of cells which have not been transformed or have lost the hybrid vector. Thus, for example, an antibiotic is added to the medium if the hybrid vector contains an antibiotic resistance gene as marker. If, for instance, a host cell is used which is auxotrophic in an essential amino acid whereas the hybrid vector contains a gene coding for an enzyme which complements the host defect, a minimal medium deficient of said amino acid is used to culture the transformed cells.

Cells of higher eukaryotic origin such as mammalian cells are grown under tissue culture conditions using commercially available media, for example Dulbecco's modified Eagle medium (DMEM), minimum essential medium, RPMI 1640 medium and the like as mentioned above, optionally supplemented with growth-promoting substances and/or mammalian sera. Techniques for cell cultivation under tissue culture condition are well known in the art and include homogeneous suspension culture, e.g. in an airlift reactor or in a continuous stirrer reactor, or immobilized or entrapped cell culture, e.g. in hollow fibres, microcapsules, on agarose microbeads, porous glass beads, ceramic cartridges, or other microcarriers.

Culturing is affected by processes which are known in the art. The culture conditions, such as temperature, pH value of the medium and fermentation time, are chosen so that a maximum titer of the polypeptide or derivative of the invention is obtained.

In order to allow selection of the transformed from the nontransformed cells, the DNA molecules of the invention carry a selection marker or, alternatively, the cells are cotransformed with a second vector containing such marker. As in other systems such selection marker is an expressible, structural gene, the expressed polypeptide of which (an enzyme) provides resistance against compounds toxic to the receipt organism or which completes the enzyme system of a mutant lacking such essential polypeptide.

Apart from the advantages of 7B2 in vivo, it surprisingly also acts as a deaggregating agent in vitro, i.e. it is able to transform inactive soluted aggregates of protein, preferably monomeric protein, into biologically active protein or to prevent the aggregation of the protein, preferably monomeric protein, to inactive aggregates.

The invention thus also provides a method for the deaggregation or prevention of aggregation of protein, preferably monomeric protein, comprising treating inactive aggregates, including soluble inactive aggregates, of the protein with 7B2 in order to produce deaggregated proteins, preferably monomeric proteins, or comprising treating deaggregated proteins, preferably monomeric proteins, with 7B2 in order to prevent the aggregation thereof. The deaggregation or prevention of aggregation of proteins is of importance because aggregation inactivates biologically active proteins or because deaggregated proteins can be refolded to active protein while the aggregates can not be refolded.

This method according to the invention is in particular characterized in that protein, preferably monomeric protein, is treated with 7B2 in order to prevent aggregation or in that aggregates of protein, preferably monomeric protein, are treated with 7B2 in order to deaggregate the protein. Treatment can take place in suitable buffer solutions, e.g. phosphate or Tris buffer, or, for example, even in supernatants of cells which have secreted the protein. For deaggregation the protein to be treated and 7B2 are mixed and incubated for a few minutes up to a few hours, for example between about 30 min and 1 h at a temperature between about 4° C. and 30° C., optionally in the presence of ATP which, if used, is preferentially used in a concentration between about 1 and 10 mM. For preventing aggregation 7B2 and the protein which should not aggregate are mixed and the protein is stored in the presence of 7B2 under usual conditions. 7B2 may also for example added to a yeast cell culture secreting the protein which should not aggregate.

For use in vitro 7B2 is prepared by genetic engineering in pro- or eukaryotic cells, for example in E. coli or yeast cells, isolated from the cells or, if the prepared 7B2 is secreted, from the supernatant, and added to the protein which is to be deaggregated or aggregation of which is desired to be prevented.

The most preferred embodiments of the present invention are those described in the examples. However, the invention is also intended to include most preferentially the obvious variants and equivalents of the specific embodiments described in the examples.

The examples are intended to illustrate the invention. However, they should not be construed as a limitation thereof.

EXAMPLES

Example 1: Production of recombinant human 7B2 in E. coli (clone pGEX-2T/7B2)

Figure 1:
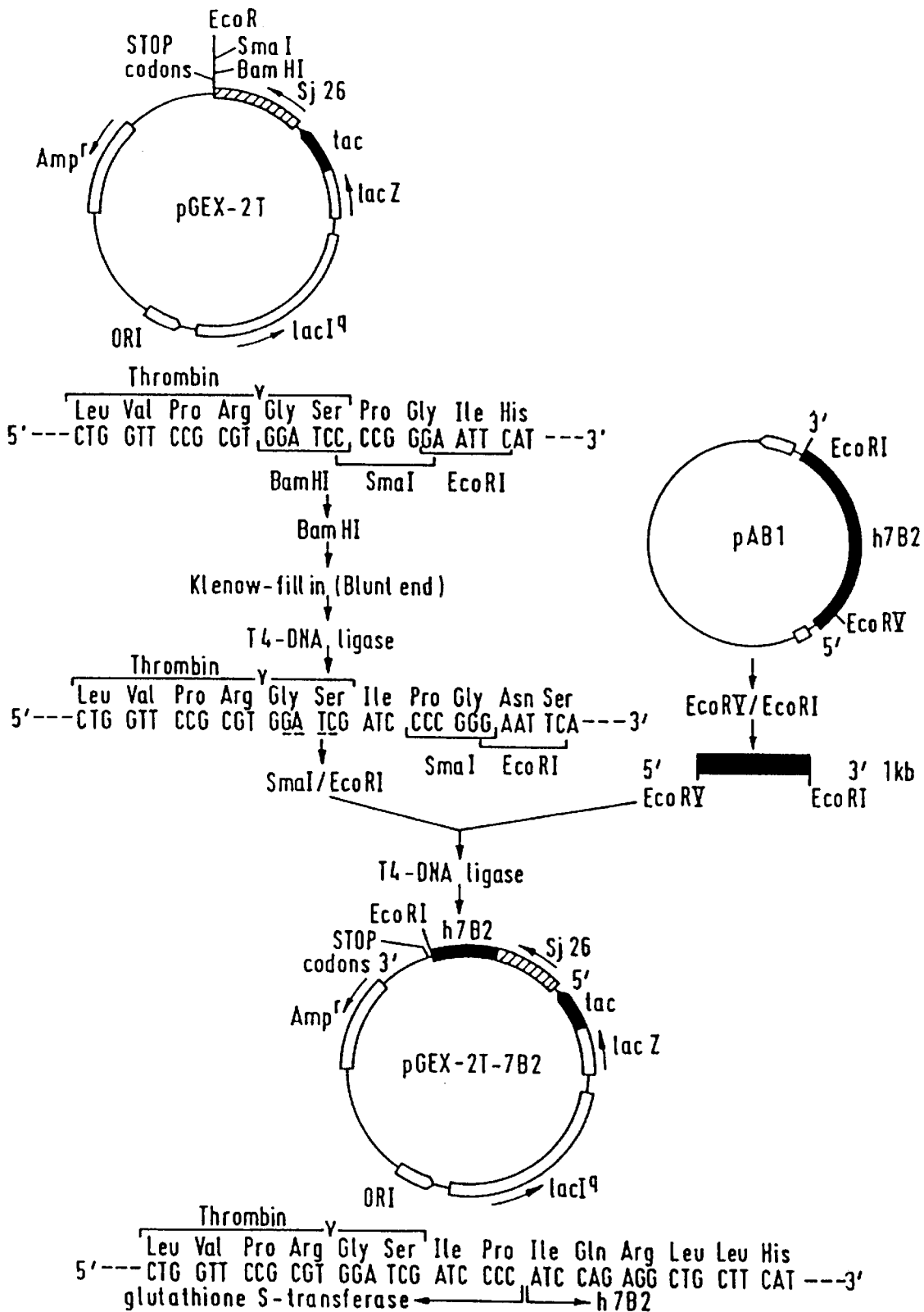
FIG. 1 illustrates the construction of the pGEX-2T-7B2 clone. The BamHI site in the MCS of the vector pGEX-2T is filled in using Klenow polymerase after which a EcoRV-EcoRI fragment of the h7B2-cDNA (from pAB1) is cloned into the SmaI/EcoRI sites. In the transitory area between Sj26 and 7B2 in the amino acid sequence of the fusion protein a recognition site for thrombin is present.
Figure 2:
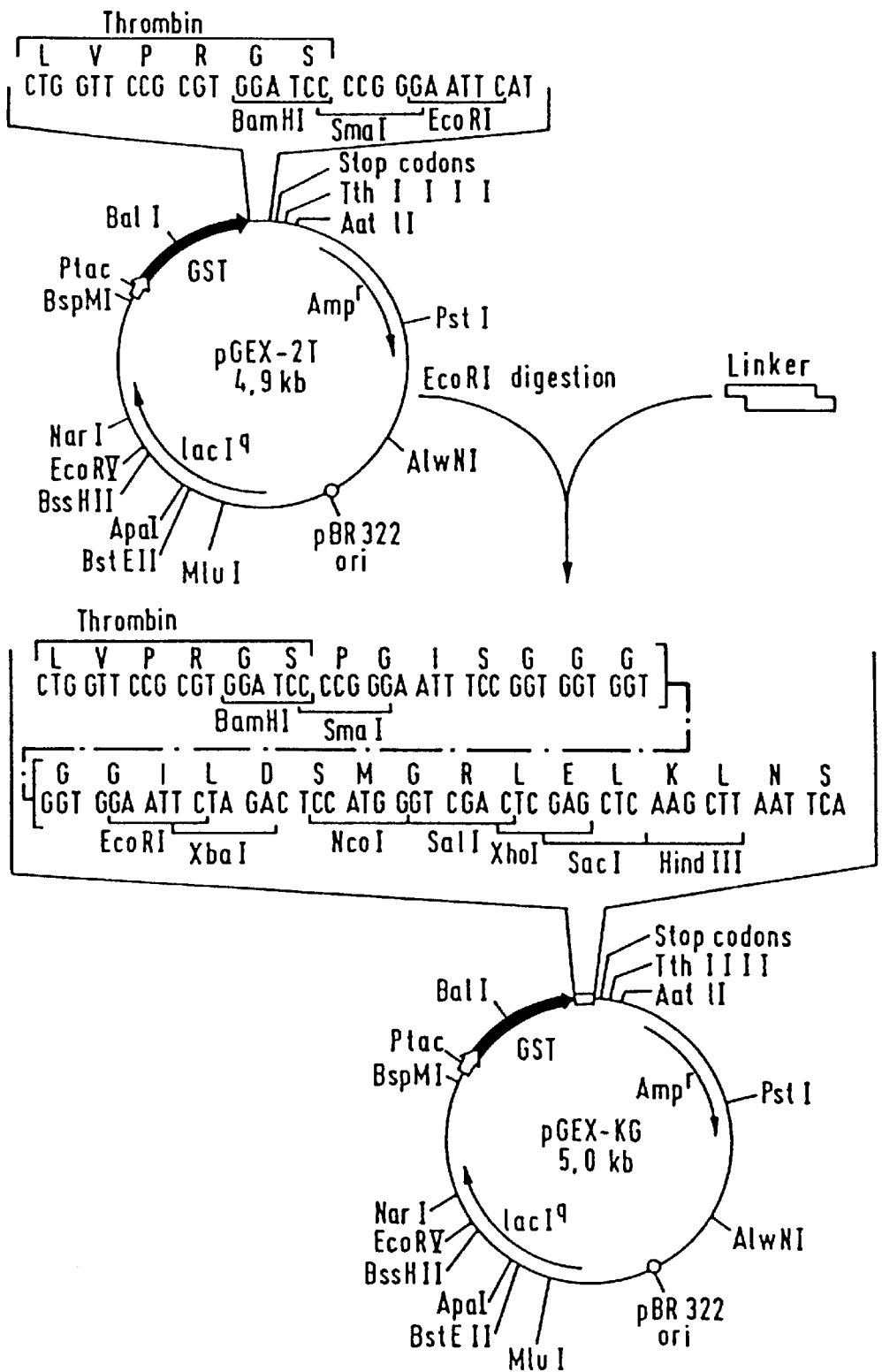
FIG. 2 illustrates the construction of the prokaryotic expression vector pGEX-KG, derived from the vector pGEX-2T by inserting a linker with multiple cloning sites in the EcoRI site.

The prokaryotic expression vector pGEX-2T (Amrad Corporation Limited, Melbourne, Vicoria, Australia) carries the glutathione S-transferase (GST) gene of Schistosoma japonicum downstream from a tac-promoter. To make this vector suitable for expression of 7B2 as a fusion protein with GST in Escherichia coli, a reading frame shift has to be introduced into the multiple cloning site at the 3' end of the GST gene. For this the pGEX-2T vector is digested with BamHI and the recessed 3' termini are filled in by use of the Klenow fragment of DNA polymerase I. Ligation of the obtained blunt ends resulted in an altered pGEX-2T vector with four additional basepairs, providing an alternative reading frame. This vector is digested with SmaI and EcoRI and a 1.0 kb EcoRV-EcoRI cDNA fragment encoding amino acids 14 to 185 of human 7B2 (for 7B2 sequence see EP-A-0 315 254) is ligated into the Sma/EcoRI sites of the modified vector. The resulting plasmid is transformed into the Escherichia coli strain JM101 hsdS recA, giving clone pGEX-2T/7B2 (see FIG. 1).

An overnight culture of bacteria containing the pGEX-2T/7B2 plasmid (clone pGEX-2T/7B2) is diluted 20-fold in 200 ml LB medium containing ampicillin (70 µg/ml) and grown for 1 h at 37° C. To induce expression of the fusion protein, IPTG (isopropyl β-D-thiogalactopyranoside; Sigma) is added to a 0.5 mM final concentration and the culture is grown for an additional 3 h. Cells are harvested by centrifugation (5 min, 5000 rpm) and lysed by sonication (10 times, 20 sec each) in 3 ml lysis buffer containing 50 mM Tris, pH 7.5; 50 mM NaCl; 1% (V/V) Triton X-100; 250 mM guanidine hydrochloride; 10% (v/v) glycerol; 1 mM ethylenediaminetetra-acetate (EDTA), 10 mM dithiothreitol (DTT) and 1 mM phenylmethylsulfonylfluoride (PMSF). The lysate is centrifuged at 5,000 rpm for 10 min at 4° C. and the fusion protein could be isolated from the supernatant by affinity chromatography with glutathione agarose (Sigma, G4510). For this the supernatant is mixed with 500 µl 50% (v/v) glutathione agarose that is equilibrated in the lysis buffer. After a 20-min incubation of the mixture with constant rotation of the sample at 4° C., the mixture is centrifuged (30 sec, 5,000 rpm) and the beads are washed three times with 3 ml of the lysis buffer and five times with 30 ml thrombin cleavage buffer (50 mM Tris, pH 5.5; 150 mM NaCl; 2.5 mM CaCl$_2$). After the last wash the beads are suspended in 500 µl thrombin cleavage buffer containing 2 µg of thrombin (from human plasma, lyophilized powder, Sigma, T6759) and the mixture is rotated for 10 min at room temperature. The cleavage reaction is stopped by adding PMSF (1 mM final concentration) and putting the sample on ice.

7B2 obtained lacks the signal peptide and the first 13 amino acids of the mature human 7B2 and contains four additional N-terminal amino acids.

To remove thrombin, 200 µl of a 50% (v/v) p-aminobenzamidine-agarose (Sigma A 7155) suspension is added to the supernatant to remove possible remainders of fusion protein. After a 10 min incubation (4° C.) the agarose beads are removed and the purified 7B2 is stored at −80° C. or lyophilized before storage at −20° C. The yield of purified (>95% pure) recombinant 7B2 is about 0.5 µg/µl. Analogous results are obtained when the pGEX-2T/7B2 construct is transformed into other E. coli strains like RR1, HB101, C600 or DH5α.

Protein samples are analyzed using 12.5% SDS-Polyacrylamide gel electrophoresis (SDS-PAGE) (Laemmli, 1970) followed by either staining of the gel in a 0.2% Coomassie Brilliant Blue R250 solution (50% methanol, 7.5% acetic acid) or subjecting the gel to Western blotting. For Western blot analysis, after separation of the proteins, the SDS-gel is equilibrated in blotting buffer (150 mM glycine, 20 mM tris, 20% methanol) for 15 min. Electrophoretic transfer of proteins onto nitrocellulose is performed in blotting buffer for 16 h at 100 mA. Blots are rinsed in phosphate buffered saline (PBS, 50 mM NaHPO$_4$, pH 7.3; 120 mM NaCl) and blocked for 1 h in blocking buffer (3% chicken egg albumin (CEA), 1% normal goat serum (NGS) and 0.3% triton in PBS). Antibody incubations are at room temperature using the anti-7B2 monoclonal antibodies MON-102 and MON-144 (culture supernatants)[van Duijnhoven, H. L. P., et al., J. Immunol. Methods, 142:187–198(1991)], diluted 1:500 in blocking buffer. After 2 h unbound material is removed by rinsing the blot 3 times in rinsing buffer (PBS with 0.5% CEA, 0.2% NGS and 0.3% triton). The nitrocellulose filter is then incubated in this buffer containing peroxidase labeled goat-anti-mouse antibodies (GAM/PO, 1:1000) for 2 h.

Example 2: Production of recombinant 7B2 genes for expression in eukaryotic cells Example 2a: Construction of the 7B2 gene encoding an amino-terminal 7B2 signal peptide and the complete human protein In order to obtain the above gene for convenient cloning in a yeast expression vector, polymerase chain reaction (PCR) is performed on the complete human cDNA encoded in the plasmid PEC7B2 [Martens, G. J. M., FEBS Letts., 234:160–164 (1988); DNA sequence of human 7B2 cDNA published in EP-A-0 315 254], using two deoxyoligoribonucleotides as primers (see SEQ ID Nos. 1 and 2). The human cDNA is amplified in 30 cycles of PCR. An EcoRI-SphI fragment containing a 54 bp 7B2 signal sequence (SEQ ID No.3), the 555 bp coding region of the 7B2 gene and a stop codon (SEQ ID No. 4) is ligated to the plasmid pUC19 [Boehringer Mannheim GmbH, Germany], completely digested with EcoRI and SphI. An aliquot of the ligation mixture is added to calcium-treated, transformation competent E. coli HB101 cells [Invitrogen, San Diego, USA]. Six ampicillin resistant E. coli transformants are grown in the presence of 100 mg/l ampicillin. Plasmid DNA is prepared and analyzed by digestion with EcoRI/SphI, EcoRI/PstI, SacI/KpnI, EcoRI/BamHI and XbaI/ HindIII. One clone with the expected restriction fragments is selected and called pUC19/EcoRI-SphI/7B2ss-7B2 [where 7B2ss denotes the 18 amino acid signal sequence of human 7B2].

Example 2b: Construction of a truncated 7B2 gene encoding an amino-terminal 7B2 signal peptide and the first 137 amino acids of the human protein In order to obtain the above gene, PCR is performed on the complete human cDNA (as in Example 2a) using two deoxyoligoribonucleotides as primers (see SEQ ID Nos. 1 and 5). The human cDNA is amplified as in Example 2a. An about 480 bp EcoRI-SphI fragment encoding the 18-amino acid 7B2 signal peptide (see Example 2a), 137 amino acids of human 7B2 and a stop codon is ligated to the plasmid pUC19, as in Example 2a Plasmid DNA is prepared from transformants and analyzed by digestion with EcoRI/SphI, EcoRI/PstI, SacI/KpnI and XbaI/HindIII. One clone with the expected restriction fragments is selected and called pUC19/ EcoRI-SphI/7B2ss-7BΔ1.

Example 2c: Construction of a truncated 7B2 gene encoding an amino-terminal 7B2 signal peptide and the first 149 amino acids of the human protein In order to obtain the above gene, PCR is performed on the complete human cDNA (as in Example 2a) using two deoxyoligoribonucleotides as primers (see SEQ ID Nos. 1 and 6). The human cDNA is amplified as in Example 2a. An about 515 bp EcoRI-HindIII fragment encoding the 18-amino acid 7B2 signal peptide (see Example 2a), 149 amino acids of human 7B2 and a stop codon is ligated to the plasmid pUC19, completely digested with EcoRI and HindIII. Plasmid DNA is prepared from transformants and analyzed by digestion with EcoRI/HindIII, EcoRI/ PstI, SacI/KpnI and XbaI/HindIII. One clone with the expected restriction fragments is selected and called pUC19/EcoRI-HindIII/7B2ss-7B2Δ2.

Example 2d: Construction of a truncated 7B2 gene encoding an amino-terminal 7B2 signal peptide and the first 170 amino acids of the human protein In order to obtain the above gene, PCR is performed on the complete human cDNA (as in Example 2a) using two deoxyoligoribonucleotides as primers (see SEQ ID Nos. 1 and 7). An about 580 bp EcoRI-HindIII fragment encoding the 18-amino acid 7B2 signal peptide (see Example 2a), 170 amino acids of human 7B2 and a stop codon is ligated to the plasmid pUC19 as in Example 2c. Plasmid DNA is prepared from transformants and analyzed by digestion with EcoRI/ HindIII, EcoRI/PstI, SacI/KpnI and XbaI/HindIII. One clone with the expected restriction fragments is selected and called pUC19/EcoRI-HindIII/7B2ss-7B2Δ3.

Example 3: Production of recombinant 7B2 in yeast cells

Example 3a: Construction of a gene encoding the amino-terminal signal peptide from the yeast SUC2 gene and the complete human 7B2

The plasmid pUC19/ BamHI-XhoI GAPDH-IT contains the 400 bp promoter region of the S. cerevisiae GAPDH gene and 57 bp of the chemically synthesized signal sequence from the S. cerevisiae SUC2 gene [hereafter referred to as the invertase signal sequence or only Invss (SEQ ID No. 8)]. The promoter and the signal sequence is linked by an EcoRI site. The plasmid is completely digested with XhoI and the sticky end is filled in with T4 polymerase. NcoI linkers are added to the the blunt-ended DNA. After digestion with BamHI and NcoI, an about 465 bp BamHI-NcoI fragment is isolated.

The plasmid PEC7B2 (see Example 2a) is completely digested with EcoRI and the sticky end is filled in with T4 polymerase. NcoI linkers are added to the the blunt-ended DNA. After digestion with SacI and NcoI an about 270 bp NcoI-SacI fragment containing the 5'end of the 7B2 gene is isolated.

The isolated about 465 bp BamHI-NcoI and the about 270 bp NcoI-SacI fragments are subcloned in the plasmid pUC19 which is completely digested with BamHI-SacI. After transformation in E. coli HB101, DNA obtained from 6 transformants are analyzed with BamHI/SacI and BamHI/ HindIII. One correct clone is named pUC19/ BamHI-SacI/ GAPDH-Invss-7B2 (inexact construction). In this construction the coding region of the invertase signal sequence is not in-frame with that of 7B2.

The exact construction containing the invertase signal sequence in-frame with the 7B2 coding region is constructed by PCR using three deoxyoligoribonucleotides primers (see SEQ ID Nos. 9, 10 and 11). The template used to perform site-directed deletion mutagenesis is pUC19/BamHI-SacI/ GAPDH-Invss-7B2 (inexact construction). Primers with SEQ ID Nos. 9 and 10 are used in the first round of PCR to obtain an about 180 bp fragment coding for a part of the invertase signal sequence in-frame with the 7B2 gene. In a second round of PCR, the denatured about 180 bp fragment obtained from the first PCR and the primer with SEQ ID No. 11 are used to obtain an about 220 bp EcoRI-SacI fragment encoding the complete invertase signal sequence in-frame with a part of the 7B2 gene (5' end of the gene). This fragment is subcloned in pUC19, completely digested with EcoRI and SacI. DNA is obtained from six E. coli HB101 transformants. Analysis reveals that all clones are correct. One such clone is named pUC19/EcoRI-SacI/Invss-7B2Sac (exact construction).

An about 220 bp EcoRI-SacI fragment encoding the complete invertase signal sequence in-frame with a part of the 7B2 gene is isolated from the plasmid pUC19/EcoRI-SacI/Invss-7B2Sac (exact construction).

An about 410 bp SacI-HindIII fragment encoding the 3' segment of 7B2 and a stop codon is isolated from the plasmid pUC19/EcoRI-SphI/7B2ss-7B2 (see Example 2a).

The EcoRI-SacI and the SacI-HindIII fragments are ligated to pUC19 which is completely digested with EcoRI and HindIII. DNA obtained from 6 transformants are analyzed with EcoRI/SacI, EcoRI/BamHI and EcoRI/ HindIII. One correct clone is designated as pUC19/ EcoRI-HindIII/ Invss-7B2. The plasmid encodes the complete invertase signal sequence (57 amino acids) in-frame with the complete human 7B2 (185 amino acids) and a stop codon.

Example 3b: Construction of the promoter from the yeast cytoplasmic cyclophilin gene The promoter from the yeast c-cyclophilin [the S. cerevisiae CYP1 gene; Haendler, B., Keller, R. Hiestand, P. C, Kocher, H. P., Wegmann, G., Movva, N. R., Gene 83:39–46 (1989)] is isolated by PCR. The PCR is performed, as in Example 2a, using genomic DNA derived from the yeast strain S288C as template and two deoxyoligoribonucleotides as primers (see SEQ ID No. 12 and No. 13). An about 545 bp BamHI-EcoRI fragment is isolated and subcloned in pUC18 which is completely digested with BamHI and EcoRI DNA obtained from 6 transformants are analyzed with restriction enzymes and DNA sequencing. One correct clone is named pUC19/BamHI-EcoRI/CYP1p.

Example 3c: Construction of an appropriate transcription terminator fragment from the yeast PHO5 gene An about 377 bp SphI-PstI fragment from the PHO5 gene [SphI linkers are added to the flushed Sau3A site at the 3' end of the PHO5 gene; Meyhack, B., Bajwa, W., Rudoph, H., Hinnen, A., EMBO J., 6, 3455–3463, (1982)], which acts as an effective transcription terminator in the expression of heterologous genes, is subcloned in pUC19, completely digested with SphI and PstI. After analysis of transformants, one correct clone is named pUC19/SphI-PstI/PHO5T.

Example 3d: Construction of a yeast expression vector for the secretion of complete 7B2 using the 7B2 signal sequence An about 545 bp BamHI-EcoRI CYP1p fragment is isolated from pUC19/BamHI-EcoRI/CYP1p (see Example 3b).

An about 620 bp EcoRI-HindIII fragment encoding the 18-aminoacid 7B2 signal peptide, 185 amino acids of the human 7B2 and a stop codon is isolated from pUC19/EcoRI-SphI/7B2ss-7B2 (see Example 2a).

An about 385 bp HindIII-SalI PHO5T fragment is isolated from pUC19/SphI-PstI/PHO5T (see Example 3c).

The BamHI-EcoRI, the EcoRI-HindIII and the HindIII-SalI fragments are ligated to the vector pDP34 which is completely digested with BamHI and SalI. The plasmid pDP34 is an *E. coli-S. cerevisiae* shuttle vector, which contains the complete *S. cerevisiae* 2-micron plasmid and encodes the *S. cerevisiae* URA3 and dLEU2 genes as yeast selection markers. After transformation in *E. coli* HB101, DNA is prepared from 24 transformants. Analysis with BamHI/SalI confirms the correct clones. One such clone is referred to as pDP34/BamHI-SalI/CYP1p-7B2ss-7B2-PHO5T.

Example 3e: Construction of the yeast expression vectors for the secretion of the truncated 7B2 using the 7B2 signal sequence The plasmids which are referred to as
pDP34/ BamHI-SalI/CYP1p-7B2ss-7B2Δ1-PHO5T
pDP34/ BamHI-SalI/CYP1p-7B2ss-7B2Δ2-PHO5T
pDP34/ BamHI-SalI/CYP1p-7B2ss-7B2Δ3-PHO5T
are constructed exactly in the way described in Example 3d. The EcoRI-HindIII fragments containing the 7B2 signal sequence, the coding region for the truncated human 7B2 genes and a stop codon are isolated from the appropriate plasmids (see Examples 2b to d).

Example 3f: Construction of a yeast expression vector for the secretion of complete 7B2 using the yeast SUC2 signal sequence An about 545 bp BamHI-EcoRI CYP1p fragment from pUC19/BamHI-EcoRI CYP1p (see Example 3b) and an about 220 bp EcoRI-SacI fragment from pUC19/EcoRI-SacI/Invss-7B2 [(exact construction); see Example 3a] is subcloned in pUC19 completely digested with BamHI and SacI as in Example 3a DNA obtaned from one correct clone is named pUC19/BamHI-SacI/CYP1p-Invss-7B2 (5' end).

An about 765 bp BamHI-SacI fragment containing the CYP1 promoter, the invertase signal sequence and the 5' end of the human 7B2 gene from the plasmid pUC19/BamHI-SacI/CYP 1p-Invss-7B2 (5' end), an about 410 bp SacI-HindIII fragment containing the 3' end of the human 7B2 gene and a stop codon from the plasmid pUC19/EcoRI-SphI/7B2ss-7B2 (see Example 2a), and an about 377 bp HindIII-SalI fragment from pUC19/ SphI-PstI/PHO5T (see Example 3c) is ligated to the vector pDP34 which is completely digested with BamHI and SalI. After transformation in *E. coli* HB101, DNA is prepared from 24 transformants. Analysis with BamHI/SalI and BamHI/HindIII confirms the correct clones. One such clone is referred to as pDP34/BamHI-SalI/CYP1p-Invss-7B2-PHO5T.

Example 3h: Construction of the yeast expression vectors for the secretion of the truncated 7B2 using the 7B2 signal sequence The plasmids which are referred to as
pDP34/ BamHI-SalI/CYP1p-Invss-7B2Δ1-PHO5T
pDP34/ BamHI-SalI/CYP1p-Invss-7B2Δ2-PHO5T
pDP34/ BawHI-SalI/CYP1p-Invss-7B2Δ3-PHO5T
are constructed exactly in the way described in Example 3f. The SacI-HindIII fragments containing the 3' end of the coding region for the truncated human 7B2 genes are isolated from the appropriate plasmids (see Examples 2b to d).

Example 3 h: Construction of pDP33/BamHI/SalI/CYP1p-Invss-7B2-PHO5T
pDP33/BamHI-SalI/CYP1p-Invss-7B2Δ1-PHO5T
pDP33/BamHI-SalI/CYP1p-Invss-7B2Δ2-PHO5T
pDP33/BamHI-SalI/CYP1p-Invss-7B2Δ3-PHO5T The above plasmids are constructed exactly in the way described in Examples 3f and g. The appropriate fragments are ligated to pDP33 which is nearly identical to pDP34, the only difference being that pDP33 lacks the *S. cerevisiae* URA3 gene present in the plasmid pDP34 as a yeast selection marker. The defective promoter encoded by dLEU2 and present in the plasmid pDP33 can help to increase the copy number of the above plasmid constructions in a yeast cell possessing a non-functional genomic copy of the LEU2 allele.

Example 3i: Transformation of the *S. cerevisiae* strain AB 110 prb1- with the plasmids encoding the human 7B2 gene Yeast transformation is carried out as described by Klebe et al. in Gene 25:333–341 (1983), and by Hinnen et al. in Proc. Natl. Acad. Sci. USA 75:1929(1978). *S. cerevisiae* AB110prb1⁻[see Example 4b; PRB1 encodes the yeast protease B gene], or as such any strain of yeast which is disrupted for the yeast proteases A and B, is transformed with the plasmids compiled hereinafter and the transformants are named as indicated:

| Plasmids | Transformant Names |
|---|---|
| pDP34I BamHI-SalI/ CYP1p-7B2ss-7B2-PHO5T | yHB1 |
| pDP34/ BamHI-SalI/ CYP1p-7B2ss-7B2Δ1-PHO5T | yHB2 |
| pDP34/ BamHI-SalI/ CYP1p-7B2ss-7B2Δ2-PHO5T | yHB3 |
| pDP34/ BamHI-SalI/ CYP1P-7B2ss-7B2Δ3-PHO5T | yHB4 |
| pDP34/ BamHI-SalI/ CYP1p-Invss-7B2-PHO5T | yHB5 |
| pDP34I BamHI-SalI/ CYP1P-Invss-7B2Δ1-PHO5T | yHB6 |
| pDP34I BamHI-SalI/ CYP1p-Invss-7B2Δ2-PHO5T | yHB7 |
| PDP34/ BamHI-SalI/ CYP1P-Invss-7B2Δ3-PHO5T | yHB8 |
| pDP33/ BamHI-SalI/ CYP1p-Invss-7B2-PHO5T | yHB9 |
| pDP33/ BamHI-SalI/ CYP1p-Invss-7B2Δ1-PHO5T | yHB10 |
| pDP33/ BamHI-SalI/ CYP1P-Invss-7B2Δ2-PHO5T | yHB11 |
| pDP33/ BamHI-SalI/ CYP1p-Invss-7B2Δ3-PHO5T | yHB12 |

Three colonies of each of the transformants are selected and designated with an additional number (viz yHB1-1, yHB1-2, yHB1-3).

Example 3j: Growth of 7B2 yeast transformants in shake-flask cultures

The S. cerevisiae strain AB110 (Matα, his 4-580, leu2, ura3-52, pep4-3, [cir°]) is disclosed elsewhere [Barr, P. J. et al., J. Biol. Chem. 263, 16471–16478 (1988)]. A minimal medium containing 8.4 g/l yeast nitrogen base without amino acids (Difco), 10 g/l L-asparagine, 1 g/l histidine and 20 g/l glucose is used as a pre-culture. This medium is supplemented with either 1 g/l leucine or 1 g/l uracil depending on the plasmid pDP34 or pDP33 one needs to select. 7B2 is expressed in the main culture containing 1.7 g/l yeast nitrogen base supplemented with 30 g/l glucose, 8.5 g/l casamino acids and the required amino acids. Yeast transformants (see Example 3i) are grown at 30° C. on a rotary shaker at 180 rev/ min for 48 h in a 10 ml volume of the pre-culture medium and for 48 h in a 60 ml volume of main culture.

Aliquot of cells are harvested and the secreted 7B2 is concentrated 10 to 50-fold using Centricon-10 filters (Amicon). The concentrated supernatants are used for incubation with the yeast culture broth containing IGF-1. Qualitative estimates of intracellular and secreted 7B2 are made by Western blotting using purified 7B2 obtained from the expression of 7B2 in E. coli (see Example 1). The monoclonal antibody MON-102 is used to recognize the 7B2 antigens (see Example 1).

Example 4: Improvement of the production of IGF-1 by means of 7B2 used in vitro or in vivo Example 4a: Transformation of S. cerevisiae with a plasmid encoding the human IGF-1 gene S. cerevisiae AB 110, i.e. a strain which has the capability to secrete the human insulin-like growth factor-i (IGF-1), is transformed with the plasmid pDP34/ GAPDHp-αFL-IGF1-αFT [Steube, K. et al., Eur. J. Biochem., 198:651–657 (1991)]. The stable 2-micron plasmid pFBY66 [European Application No. 91810124.7] containing the IGF-1 expression cassette present in pDP34/GAPDHp-αFL-IGF1-αFT is also transformed in AB110. The transformants are generically named yIGF.

Example 4b: Co-transformation of S. Cerevisiae with plasmids encoding the human IGF-1 gene and the human 7B2 gene S. cerevisiae AB110 prb1⁻ i.e. a strain which is disrupted for the yeast preoteases A and B, is co-transformed with the the plasmid pFBY66 (see Example 4a) and any of the following four plasmids pDP33/BamHI-SalI/CYP1p-Invss-7B2-PHO5T
pDP33/BamHI-SalI/CYP1p-Invss-7B2Δ1-PHO5T
pDP33/BamHI-SalI/CYP1p-Invss-7B2Δ2-PHO5T
pDP33/BamHI-SalI/CYP1p-Invss-7B2Δ3-PHO5T (see Example 3h). The transformants have the generic name yIGF/7B2.

Example 4c: Growth of yIGF in shake-flask cultures and quantitative determination of the IGF-1 protein by high performance liquid chromatography (HPLC)

Yeast transformants yIGF are grown in a rich medium containing 6.5 g/l yeast extract, 4.5 g/l casamino acids and 20 g/l glucose is used as non-selective pre-culture medium. IGF-1 is expressed in the main culture medium identical to the medium used for the expression of 7B2 (see Example 4a).

Aliquots of cells are harvested and the secreted, active monomeric IGF-1 molecule in the culture medium is measured by HPLC and ELISA [Steube, K., et al., Eur. J. Biochem., 198:651–657(1991)].

Example 4d: Growth of yIGF/7B2 in shake-flask cultures and determination of the IGF-1 protein by Western blotting Yeast transformants yIGF/ 7B2 (see Example 4b) are grown as in Example 4c. Aliquots of cells are harvested and monomeric IGF-1 is estimated by Western blotting. It appears that the amounts of reduced monomeric IGF-1 obtained from yIGF/7B2 is more than that from yIGF (see Example 4a).

Example 4e: Effect of 7B2 on the titres of active, monomeric IGF-1

Concentrated supernatants of 7B2 (see Example 4b) are incubated with the yeast culture supematant containing IGF-1 (see Example 3j), in the presence or absence of ATP (final concentration 1 mM to 10 mM), at 30° C. for 1 h. Titres of active monomeric IGF-1 is measured by HPLC. The same culture supernatants are incubated at 30° C. in the absence of 7B2 but in the presence of ATP, and also in the absence of both 7B2 and ATP. Comparison of HPLC values reveal that after incubation of culture supernatants with 7B2, in the presence of ATP, there is a substantial increase of IGF-1 titres.

Typically, 60 μl of yeast culture supernatant (containing 2.5 μg of active IGF-1 monomer and 20 μg of inactive molecules) is incubated with 60 μl of 20-fold concentrated 7B2 supernatant (containing 5 μg of truncated 7B2), secreted from yHB6, yHB7, yHB10 and yHB11, in the presence of 6 μl of 200 mM ATP for 1 h at 30° C., followed by the addition of EDTA (final concentration 2 mM). 100 μl of this mixture is analyzed by HPLC.

Example 5: Improvement of the production of POMC by means of 7B2

Example 5a: Production of pure POMC protein and in vitro deaggregation

The recombinant POMC protein is produced by standard molecular biological techniques. Analogously pure POMC is obtained by cloning POMC cDNA in vector pGEX-KG. Vector pGEX-KG is a modified version of the pGEX-2T vector, in which a linker is incorporated comprising multiple cloning sites (FIG. 3). Use is made of this vector by cultivating a pBluescript clone isolated from a hypophysis library, said clone comprising POMC cDNA and removing the POMC cDNA from this clone by digesting with EcoRI and XhoI. This 1 kb EcoRI-XhoI fragment is cloned in the EcoRI and XhoI sites of the vector pGEX-KG. This clone is named pGEX-KG-POMC. Expression of this clone gave pure GST-POMC fusion protein and after cleaving with thrombin gave pure POMC. Aggregated recombinant POMC in 150 μl 50 mM Tris-HCl, pH 7.5, containing 150 mM NaCl and 2.5 mM $CaCl_2$ is incubated together with recombinant 7B2 and without for 45 min on ice. Native gel electrophoresis reveals that the addition of 7B2 resulted in a substantial increase in the amount of deaggregated POMC.

Example 5b: In vitro deaggregation of radiolabelled, newly synthesized aggregated POMC The ability of 7B2 to deaggregate the prohormone proopiomelanocortin (POMC) is tested by incubating 7B2 with newly synthsized POMC, a protein which is more than 90% of the newly synthesized total proteins produced by Xenopus intermediate pituitary cells in tissue culture. The interaction of 7B2 with aggregated POMC is analysed on native polyacrylamide gels and with HPLC.

Newly synthesized POMC is produced by neurointermediate lobes (intermediate pituitary cells) of black-adapted Xenopus during a 1 incubation of the lobes in medium containing 5 mCi/ml of [$^{35}$S]-methionine. Proteins are acid extracted with 1N HCl, freeze dried and redissolved in 150 μl 150 mM NaCl, 2.5 mM CaCl2, 50 mM Tris-HCL, pH 7.5. To 30 μl aliquots of the radiolabelled proteins (containing about 1 μg of POMC) 5 μg of either recombinant 7B2

(prepared according to Example 1), GroEL, BSA (Sigma) or α-crystallin is added and the samples are incubated for 45 min on ice.

Samples are mixed with an equal volume of gel loading buffer and are electrophoresed on a 6–25% acrylamide, 0.2–0.15% bis-acrylamide, non-denaturing gradient gel at 100 V for 3 h, followed by fixation and drying of the gel for autoradiography. Non-radiolabelled proteins are detected by staining with Coomassie blue. To confirm that virtually all of the radioactivity found in the bands on the native gel corresponds to newly synthesized POMC, the bands are excised from the dried gel and rehydrated by overlaying with 1M Tris-HCL, pH 8.0, for 1 h. Subsequently the Tris buffer is replaced with SDS sample buffer, and the samples are boiled and placed on a 12.5% SDS-polyacrylamide gel.

The acid extraction method used for the preparation of the radiolabelled proteins from Xenopus intermediate pituitary cells gives denatured (aggregated) POMC which does not enter native gels, and does not refold spontaneously under the conditions used and within the time frame of the experiments. Incubation of the aggregated POMC with recombinant 7B2 (prepared according to Example 1), however, results in a conversion of most of the aggregate to a radiolabelled band of about 120K in the native gel while incubation with GroEL led to the conversion of only part of the aggregate to a band of about 50K. Incubations with the mesophilic protein bovine serum albumin or the oligomeric protein α-crystalline has no effect. Excision of the radiolabelled bands from the native gel followed by SDS-PAGE confirms that the bands consist of monomeric 37K POMC.

Denatured radiolabelled POMC and 7B2-treated radiolabelled POMC are also analysed by HPLC (Model SP8750, Spectra Physics) on a UltraSherogel column (SEC 2000, Beckman) with 100 mM $KH_2PO_4$, 100 mM $Na_2SO_4$ (pH 7.0) as the column elution buffer at a flow rate of 1 ml/min. Radioactive fractions are counted with a β-counter. Also with this detection method a significant increase in monomeric POMC is found after incubation with 7B2.

Example 5c: In vivo-action of 7B2: Coexpression of 7B2 and POMC in higher eukaryotic cells equipped with the regulated pathway for protein secretion For the production of 7B2 and POMC in eukaryotic cells the eukaryotic expression vector pECV5-Xho is used. This vector with a length of 6.8 kb is derived from the vector pECV5 described in the article "Construction and properties of an Epstein-Barr-virus derived cDNA expression vector for human cells", P. B. G. M. Belt et al., Gene 84, 407–417 (1989). The SstI restriction site in the cloning site of pECV5 is replaced by a XhoI restriction site in the vector pECV5-Xho.

The vector pECV5-Xho comprises the Rous Sarcoma Virus (RSV) promoter followed by cloning sites and a β-globin intron and a polyadenylation signal for efficient polyadenylation. The RSV promoter is generally strongly active and certainly so in the AtT20 cells that are used. The pECV5-Xho vector provides resistance against the antibiotic hygromycin for cells after transfection as it comprises a hygromycin resistance gene within the structure.

A 0.8 kb human 7B2 cDNA fragment coding for the mature protein 7B2 is cut from the 7B2 cDNA comprising vector pAB1 via digestion with KpnI and XhoI and ligated in the KpnI-XhoI sites of the pECV5-Xho vector. This resulted in the clone pECV5-Xho-7B2. Analogously a 1.1 kb EcoRI-EcoRI POMC cDNA fragment encoding the mature POMC protein is incorporated in the correct orientation behind the RSV promoter in the EcoRI site of the vector. Plasmids pECV5-Xho-7B2 and pECV5-Xho-POMC are transfected to AtT20 cells by electroporation of 2–15 μg DNA. AtT20 is a tumor cell line derived from the anterior lobe of the mouse hypophysis. One day after the transfection the selection is started by incubating the cells in hygromycin comprising (80 μg/ml) culture medium. Two weeks later individual clones could be isolated and these grew to stable transfected AtT20 cell lines.

With the aid of Northern blot analysis and immunoprecipitation with monoclonal and polyclonal antibodies it could be determined that overproduction of 7B2 and POMC, in fact a 20- to 30-fold increase at both RNA and protein level occurred in these cells. The transfections of these constructs has no influence on the cell growth rates. As expected a greater rise in 7B2 is determined in the cells transfected with 7B2 cDNA, indicating that more 7B2 has gone to the regulated route; this 7B2 will therefore only leave the cell when this is stimulated to excrete. This is indeed found after stimulation of the cells with 5 mM 8-Br-cAMP.

The production of ACTH by cells transfected with both POMC and 7B2 could by means of a ACTH radioimmuno assay be compared with the ACTH production of cells solely transfected with POMC.

Melanotropic cells of the pars intermedia of the hypophysis are cells that express the prohormone POMC in coordination with 7B2, i.e. when POMC expression is increased 7B2 will also be produced at an increased rate. For studying the possibility that 7B2 is a heat-shock protein melanotropic cells of the hypophysis of the clawed frog *Xeopus laevis* are incubated at the normal incubation temperature of these cells (viz. 21° C.) and a same amount of cells is incubated at 30° C. (heat shock) for one hour in the presence of [$^3$]H-lysine. The amount of produced POMC is approximately the same in both cells, however in the heat-shock cells significantly more 7B2 (approximately 5 times as much) is produced; the produced 7B2 is specifically demonstrated with a monoclonal antibody against 7B2. This shows that 7B2 is indeed a heat-shock protein.

According to a known synthesis technique parts of synthetic single strand DNA (oligonucleotides) directed against the nucleotide sequence of the protein coding portion of 7B2 mRNA (i.e. 7B2 antisense oligonucleotides) are made. These antisense oligonucleotides could be used to block the translation of the 7B2 mRNA to 7B2 in the cell: as the antisense oligonucleotides bind to the mRNA the protein cannot be read or the RNA is broken down in the cell by specific RNAases. Therefore, the influence of such a blockage of the production of 7B2 on the production of biologically active compounds can be studied. These experiments can analogously be extended to AtT20 cells treated with the 7B2 anti-sense oligonucleotides.

We claim:

1. A method for the correct folding, deaggregation or prevention of aggregation of a monomeric protein in vivo comprising:

(a) constructing a host cell transformed with (i) a first DNA encoding a polypeptide having the amino acid sequence of a bioactive protein or a precursor thereof, wherein said polypeptide or precursor can aggregate within the cell to result in a multimeric, non-bioactive protein or precursor thereof and (ii) a second DNA which enable the cell to co-express human 7B2 with the said polypeptide or precursor, (b) growing said host cell for sufficient time under conditions wherein said first DNA and said second DNA express said bioactive protein and said 7B2, respectively; and (c) obtaining monomeric protein that is a bioactive protein.

2. A method according to claim 1 in which a eukaryotic host cell is used.

3. A method according to claim 2 in which a eukaryotic host cell is used which has a regulated route of protein transport and secretion.

4. A method according to claim 3 wherein said essentially monomeric protein that is bioactive is secreted.

5. A method according to claim 4 in which a precursor of said polypeptide is expressed and treated in such manner that the secreted polypeptide is a bioactive protein.

6. A method according to claim 3 in which a neuronal or endocrine cell is used.

7. A method according to claim 2 in which a yeast cell is used as host.

8. A method according to claim 7 in which the cell is transformed with a DNA sequence capable of expressing a polypeptide having the amino acid sequence of a bioactive protein.

9. A method according to claim 8, characterized in that the polypeptide having the amino acid sequence of a bioactive protein is secreted.

10. A method according to claim 1, characterized in that the bioactive protein is selected from the group consisting of peptide hormones, neuropeptides, growth factors and coagulation factors.

11. A method according to claim 10, characterized in that the bioactive protein is selected from the group consisting of a peptide hormone and neuropeptide.

12. A method according to claim 11, characterized in that the bioactive protein is IGF-1.

13. A transformed host cell transformed with (a) a first DNA encoding a polypeptide having the amino acid sequence of a bioactive protein or a precursor thereof, wherein said polypeptide or precursor can aggregate within the cell to result in a multimeric, non-bioactive protein or precursor thereof and (b) a second DNA which enables the cell to co-express human 7B2 with the said polypeptide or precursor, such that monomeric protein that is a bioactive protein is produced.

14. A transformed cell according to claim 13 which is a eukaryotic cell.

15. A transformed cell according to claim 14 which is a eukaryotic cell which has a regulated route of protein transport and secretion.

16. A transformed cell according to claim 14 which is a yeast cell.

17. A transformed cell according to claim 13, characterized in that the bioactive protein is selected from the group of peptide hormones, neuropeptides, growth factors and coagulation factors.

18. A transformed cell according to claim 17, characterized in that the bioactive protein is a peptide hormone or a neuropeptide.

19. A transformed cell according to claim 13, characterized in that the bioactive protein is IGF-1.

* * * * *